(12) United States Patent
Sholev et al.

(10) Patent No.: US 8,920,370 B2
(45) Date of Patent: Dec. 30, 2014

(54) HERNIA REPAIR DEVICE

(75) Inventors: Mordehai Sholev, Menashe (IL); Ibrahim Matter, Haifa (IL); Ziv Tamir, Moshav Lapid (IL)

(73) Assignee: Davol, Inc. (a C.R. Bard Company), Warwick, RI (US)

( * ) Notice: Subject to any disclaimer, the term of this patent is extended or adjusted under 35 U.S.C. 154(b) by 769 days.

(21) Appl. No.: 11/577,343

(22) PCT Filed: Oct. 9, 2005

(86) PCT No.: PCT/IL2005/001070
§ 371 (c)(1),
(2), (4) Date: Apr. 16, 2007

(87) PCT Pub. No.: WO2006/040760
PCT Pub. Date: Apr. 20, 2006

(65) Prior Publication Data
US 2007/0260179 A1    Nov. 8, 2007

(30) Foreign Application Priority Data

Oct. 14, 2004   (IL) .......................................... 164591

(51) Int. Cl.
*A61M 29/00* (2006.01)
*A61B 17/08* (2006.01)
*A61F 2/02* (2006.01)
*A61F 2/00* (2006.01)

(52) U.S. Cl.
CPC ....... *A61F 2/0063* (2013.01); *A61F 2002/0072* (2013.01); *A61F 2220/0016* (2013.01)
USPC .......................... 604/103; 606/151; 623/23.72

(58) Field of Classification Search
CPC .......... A61F 2/0063; A61F 2/02; A61L 31/00
USPC .......................... 606/151; 623/23.72; 604/103
See application file for complete search history.

(56) References Cited

U.S. PATENT DOCUMENTS 460,940 A    10/1891   Baugh
3,857,395 A    12/1974   Johnson et al.
(Continued)

FOREIGN PATENT DOCUMENTS

EP    0 557 963 A1    9/1993
EP    1336391          8/2003
(Continued)

OTHER PUBLICATIONS

International Search Report for Application No. PCT/IL2005/001070 mailed Apr. 14, 2008.

(Continued)

*Primary Examiner* — Gregory Anderson
*Assistant Examiner* — Christina Lauer
(74) *Attorney, Agent, or Firm* — Wolf, Greenfield & Sacks, P.C.

(57) ABSTRACT

A method and device for treating hernia by implanting at least one collapsible hernia repair patch, such as a planar mesh body at least partially enveloped by one or more elastic collars. A posterior end of an applicator carrying the repair patch may be inserted through a hernia and into the wall of the abdominal cavity, and the patch may be released into the cavity, e.g., so as to helically deploy the patch such that the patch lies in parallel to the abdominal wall. A balloon, which is removably attached to the patch, may be inflated to help move the patch to a deployed configuration, and thereafter the balloon removed from the hernia site.

16 Claims, 26 Drawing Sheets

(56) References Cited

U.S. PATENT DOCUMENTS

| | | | |
|---|---|---|---|
| 4,685,447 A * | 8/1987 | Iversen et al. | 128/899 |
| 4,769,038 A * | 9/1988 | Bendavid et al. | 623/13.11 |
| 4,823,815 A * | 4/1989 | Watson et al. | 128/897 |
| 5,176,692 A * | 1/1993 | Wilk et al. | 606/151 |
| 5,263,969 A | 11/1993 | Phillips | |
| 5,350,388 A * | 9/1994 | Epstein | 606/154 |
| 5,366,460 A * | 11/1994 | Eberbach | 606/151 |
| 5,370,650 A * | 12/1994 | Tovey et al. | 606/151 |
| 5,395,383 A | 3/1995 | Adams et al. | |
| 5,397,332 A | 3/1995 | Kammerer et al. | |
| 5,405,360 A | 4/1995 | Tovey | |
| 5,575,759 A | 11/1996 | Moll et al. | |
| 5,607,443 A * | 3/1997 | Kieturakis et al. | 606/192 |
| 5,702,416 A * | 12/1997 | Kieturakis et al. | 606/193 |
| 5,769,864 A * | 6/1998 | Kugel | 606/151 |
| 5,797,960 A | 8/1998 | Stevens et al. | |
| 5,824,082 A * | 10/1998 | Brown | 623/11.11 |
| 5,836,961 A * | 11/1998 | Kieturakis et al. | 606/190 |
| 5,957,939 A | 9/1999 | Heaven et al. | |
| 6,171,318 B1 * | 1/2001 | Kugel et al. | 606/151 |
| 6,174,320 B1 * | 1/2001 | Kugel et al. | 606/151 |
| 6,176,863 B1 * | 1/2001 | Kugel et al. | 606/151 |
| 6,224,616 B1 * | 5/2001 | Kugel | 606/151 |
| 6,258,113 B1 | 7/2001 | Adams et al. | |
| 6,302,897 B1 | 10/2001 | Rousseau | |
| 6,312,442 B1 * | 11/2001 | Kieturakis et al. | 606/190 |
| 6,379,368 B1 | 4/2002 | Corcoran et al. | |
| 6,488,653 B1 | 12/2002 | Lombardo | |
| 6,565,590 B2 | 5/2003 | Kieturakis | |
| 6,638,292 B2 | 10/2003 | Adams | |
| 6,679,900 B2 | 1/2004 | Kierturakis | |
| 6,685,714 B2 * | 2/2004 | Rousseau | 606/151 |
| 6,755,868 B2 | 6/2004 | Rousseau | |
| 6,866,676 B2 | 3/2005 | Kierturakis | |
| 6,913,614 B2 | 7/2005 | Marino et al. | |
| 7,048,698 B2 | 5/2006 | Whalen et al. | |
| 7,101,381 B2 | 9/2006 | Ford et al. | |
| 7,128,073 B1 | 10/2006 | van der Burg et al. | |
| 7,235,042 B2 | 6/2007 | Vanden Hoek et al. | |
| 7,273,489 B2 | 9/2007 | Boudjemline | |
| 7,544,213 B2 * | 6/2009 | Adams | 623/23.72 |
| 7,780,683 B2 | 8/2010 | Roue et al. | |
| 7,947,054 B2 | 5/2011 | Eldar et al. | |
| 8,500,762 B2 | 8/2013 | Sholev et al. | |
| 2003/0004581 A1 | 1/2003 | Rousseau | |
| 2004/0073257 A1 * | 4/2004 | Spitz | 606/220 |
| 2004/0092970 A1 | 5/2004 | Xavier | |
| 2004/0097792 A1 | 5/2004 | Moll et al. | |
| 2004/0167557 A1 | 8/2004 | Kieturakis et al. | |
| 2004/0236363 A1 | 11/2004 | Kieturakis | |
| 2005/0033318 A1 | 2/2005 | Miller | |
| 2007/0066980 A1 | 3/2007 | Leahy | |
| 2007/0100369 A1 | 5/2007 | Cragg et al. | |
| 2008/0033461 A1 | 2/2008 | Koeckerling et al. | |
| 2008/0065229 A1 | 3/2008 | Adams | |
| 2009/0254103 A1 | 10/2009 | Deutsch | |
| 2010/0069947 A1 | 3/2010 | Sholev et al. | |
| 2010/0292718 A1 | 11/2010 | Sholev et al. | |
| 2011/0112560 A1 | 5/2011 | Sholev | |
| 2013/0218179 A1 | 8/2013 | Sholev et al. | |

FOREIGN PATENT DOCUMENTS

| | | |
|---|---|---|
| EP | 1454599 | 9/2004 |
| GB | 2397239 | 7/2004 |
| JP | 2000-501634 A | 2/2000 |
| JP | 2007-275203 A | 10/2007 |
| JP | 2008-520372 A | 6/2008 |
| WO | WO 95/30374 | 11/1995 |
| WO | WO 96/00531 A1 | 1/1996 |
| WO | WO 97/21461 A1 | 6/1997 |
| WO | WO 2005/046511 A2 | 5/2005 |
| WO | WO 2006/040760 A2 | 4/2006 |
| WO | WO 2006/055823 A2 | 5/2006 |
| WO | WO 2009/050717 A2 | 4/2009 |

OTHER PUBLICATIONS

International Preliminary Report on Patentability for Application No. PCT/IL2005/001070 issued Mar. 24, 2009.

European Search Report from corresponding European application EP 05796121 mailed Sep. 24, 2010.

* cited by examiner

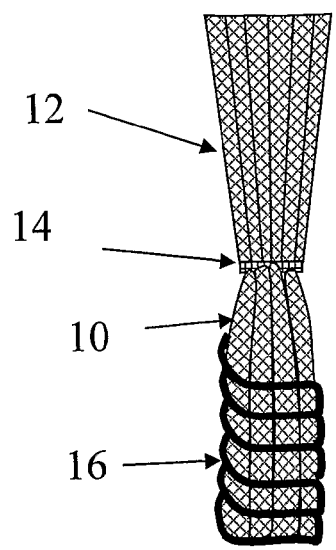
Fig. 6b
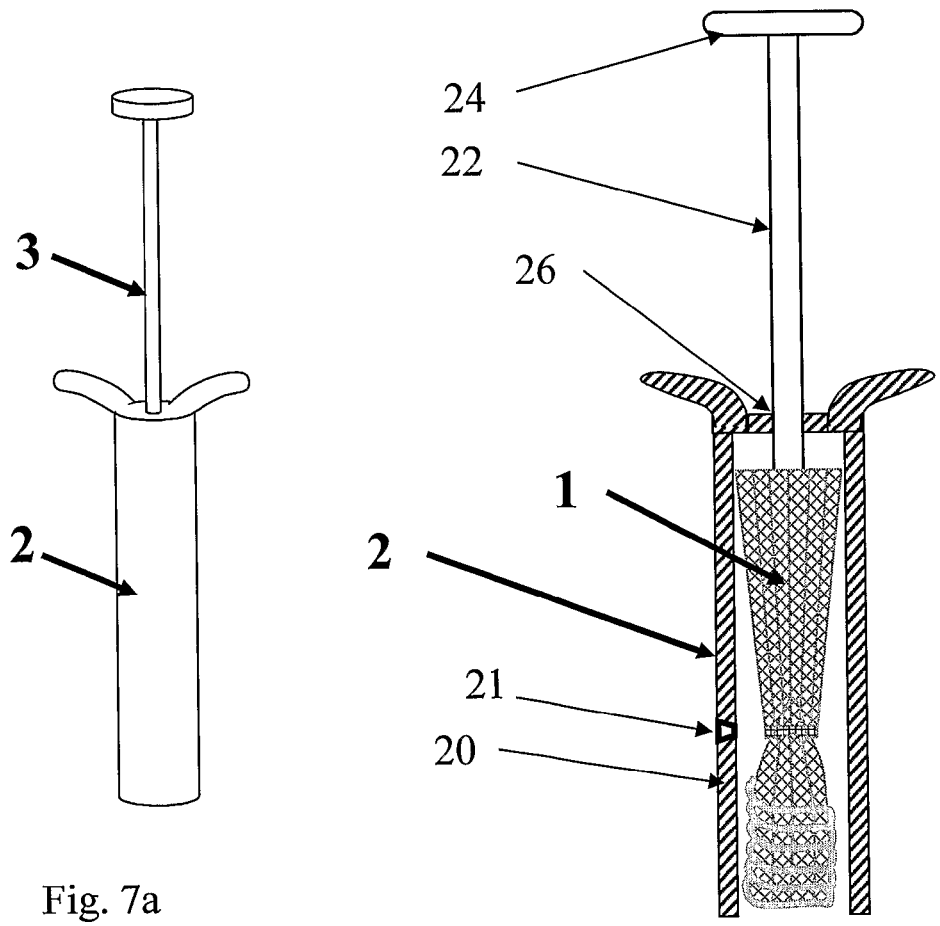
Fig. 7a
Fig. 7b

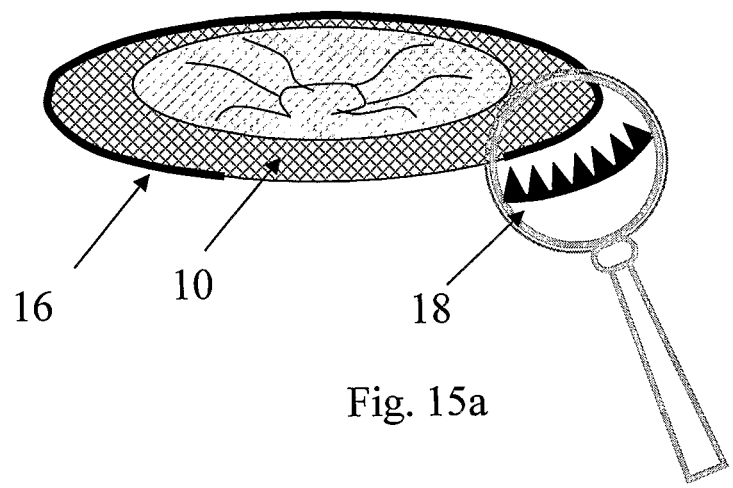
Fig. 15a
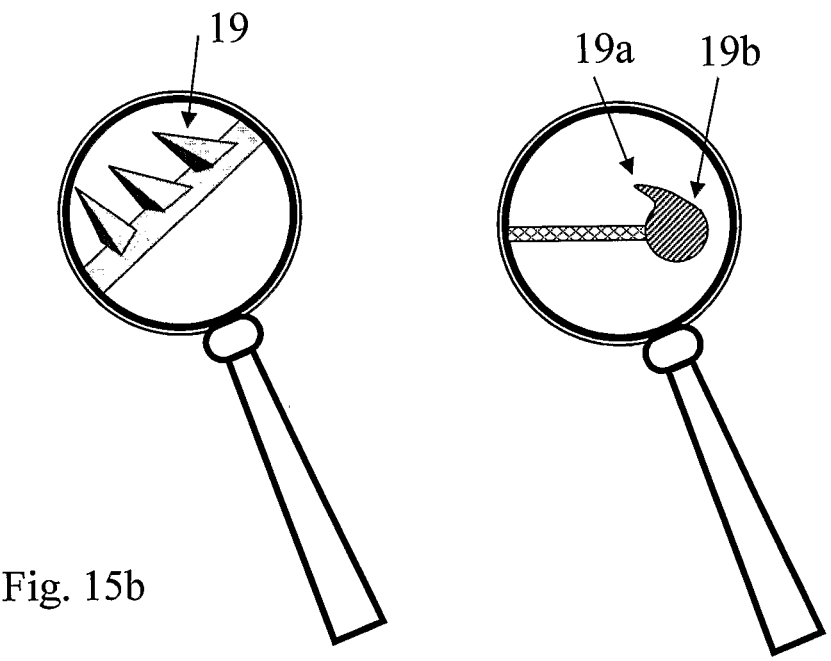
Fig. 15b
Fig. 15c

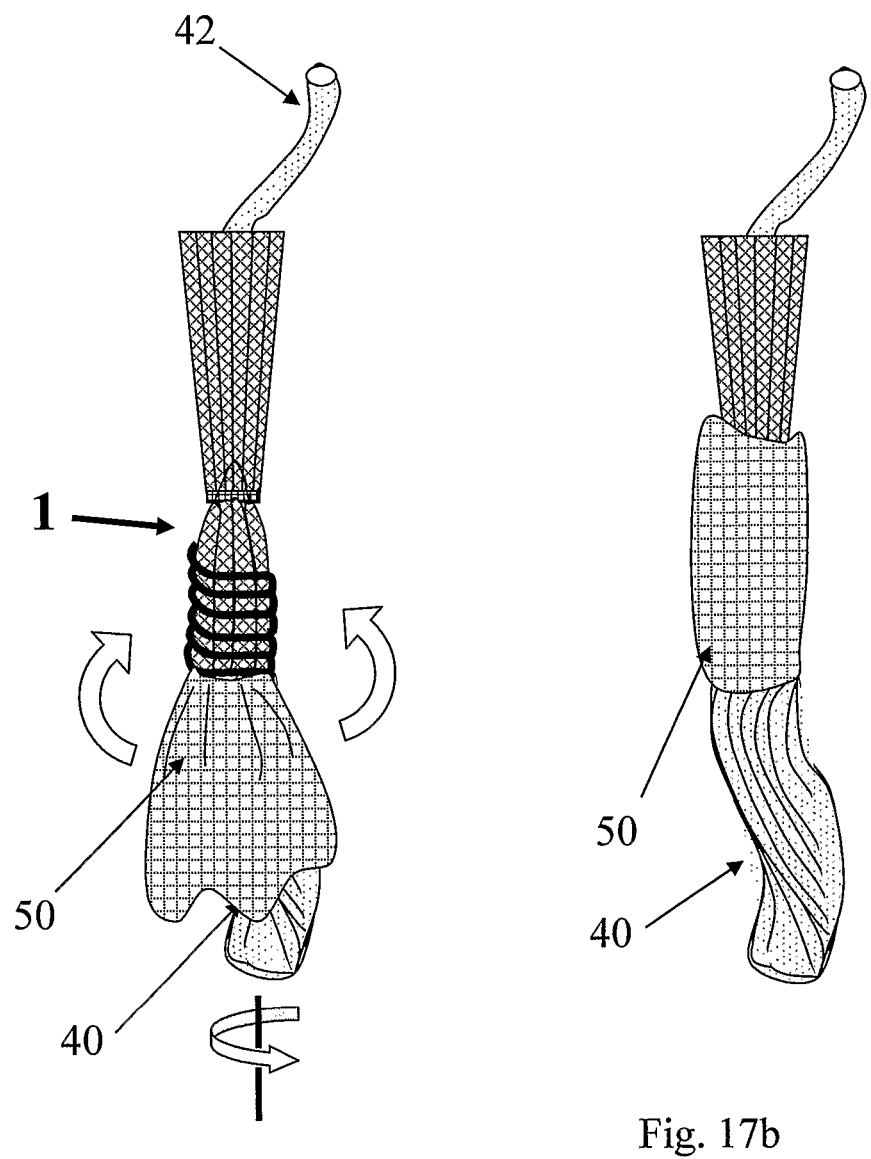

HERNIA REPAIR DEVICE

RELATED CASE INFORMATION

This application is a 371 U.S. National Stage of International Application No. PCT/IL2005/001070, filed on Oct. 9, 2005, which claims the benefit of Israel Application No. 164591, filed on Oct. 14, 2004.

FIELD OF THE INVENTION

The present invention generally related to hernia repair device and a method of using the same.

BACKGROUND OF THE INVENTION

Hernia, denoted hereinafter for umbilical hernia, ventral hernia, postoperative ventral hernia epigastric hernia, spiegelian hernia etc is a common medical condition in which an organ protrudes through an opening in its surrounding walls (especially in the abdominal region). The hernia is sometimes treated in a tension free repair, such as implementation of meshes, inflatable bladders etc. This procedure requires the insertion of the wide patch via a relatively small aperture such that the mesh is located in a posterior layer parallel to the abdominal wall. The insertion of the mesh implants to the abdominal wall by means laparoscopic technique or similar medical procedures requires puncturing of the wall providing more than one aperture is provided. Those procedures require anesthesia and usually demand a respectively long healing time.

Few techniques are suggested in the literature disclosing mesh-like or bladder implants for treating hernia. Those techniques fail to guarantee even, complete and smooth deployment of the mesh, without formation of wrinkles, and cannot ensure full anchoring of the implant to the abdominal wall. Means and method for inserting a mesh via a single small-bore opening in such manner is thus still a long felt need.

SUMMARY OF THE INVENTION

It is thus a first goal of the present invention to disclose a novel method of treating hernia by means of implanting at least one collapsible mesh rolled in an elongate open-bored applicator comprising anterior portion terminated outside the body and posterior portion located inside the body. The method is comprised of the steps of inserting the posterior end of the applicator throughout the hernia into the wall of the abdominal cavity; releasing said mesh into said cavity while helically deploying the same such that said mesh is lying in parallel to said wall; and then ejecting said applicator.

Another goal is providing a useful driving force for actuating and thrusting the helically deployed mesh. In this method, the applicator further comprises at least one inflatable balloon. The method comprising inserting said applicator throughout the hernia into the wall of the abdominal cavity; releasing at least one mesh into said cavity while helically deploying the same, such that said mesh is laying in parallel to said wall; inflating said balloon to a predetermined size, hence thrusting optionally while fastening the mesh to the posterior abdominal wall, while before or after deflating said balloon and evacuating it throughout said applicator; and then removing said applicator.

Another goal is to discloses an implantable means for treating hernia, comprising an elongate open-bored applicator having an anterior portion terminated outside the body and a posterior portion terminated with an orifice insertable via the hernia into the abdominal cavity; at least one collapsible mesh rolled in said applicator, adapted to be deployed helically when injected outside the applicator (posterior mesh); and injecting means adapted to push said mesh throughout said open bore via said posterior orifice; comprising a maneuverable pistol and handle operating the same.

BRIEF DESCRIPTION OF THE FIGURES

In order to understand the invention and to see how it may be implemented in practice, a plurality of preferred embodiments will now be described, by way of non-limiting example only, with reference to the accompanying drawings, in which FIGS. 1a to 1d schematically present two meshes and their implementing view according to one embodiment of the present invention;

FIGS. 6a to 6b schematically present two rolled meshes according to another embodiment of the present invention;

FIGS. 7a to 7c schematically present various mechanisms applicators with rolled meshes according to another embodiment of the present invention;

FIGS. 15a to 15c schematically present various fastening means according to another embodiment of the present invention;

FIGS. 17a to 17c schematically present sleeve attached to the balloon perimeter and a method collapsing the same according to another embodiment of the present invention; and, FIGS. 18a to 18d schematically present a method utilizing a sleeve according to another embodiment of the present invention.

DETAILED DESCRIPTION OF THE EMBODIMENTS

Figure 1A:
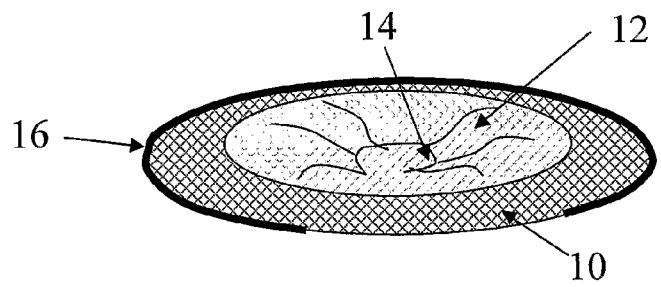

The following description is provided, alongside all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide means and method of treating hernia by means of helically deploying a mesh rolled in an applicator.

The term 'mesh' refers hereinafter in anon-limiting manner to a flexible member characterized by a plane body portion and an elastic rim (collar). The plane body portion is either a two-dimensional sheet-like member or a three-dimensional inflatable bladder-like member. The mesh is preferably characterized by either complete or incomplete circular, oval, and/or polygonal contour. According to one embodiment of the present invention, the mesh, as well as other ingredients of the device hereto defined and described, is selected in anon limiting manner for biocompatible compositions selected from polymeric compositions; glassware; titanium containing, stainless steel, nitinol, and or other metal ware; composite materials; cardboard, natural fiber, silicone, rubber or rubber-like compositions or any mixture thereof.

The present invention provides a novel method of repairing hernia by means of implanting at least one collapsible mesh rolled in an elongate open-bored applicator. This applicator is characterized by an anterior portion terminated outside the body and by posterior portion located inside the body. This method comprising inter alia the following: (a) inserting the posterior end of the applicator throughout the hernia into the wall of the abdominal cavity; (b) releasing said mesh into said cavity while helically deploying the same such that said mesh is laying in parallel to said wall; and finally (c) ejecting said applicator.

It is according to one embodiment of the present invention wherein the applicator comprising at least one posterior and at least one anterior collapsible meshes. Those two or more meshes are interconnected in their central portion by means of a connector lying inside the hernia. Thus, the aforesaid method comprising inter alia the following: (a) inserting said applicator throughout the hernia into the wall of the abdominal cavity; (b) releasing said posterior mesh into said cavity while helically deploying the same such that said mesh is laying in parallel to the posterior portion of said wall; (c) at least partially ejecting said applicator to an anterior into mesh anterior said deploying (d) and, location; predetermined said cavity such that it is laying in parallel to the anterior portion of said wall.

It is according to yet another embodiment of the present invention wherein the balloon (and/or the posterior mesh) is in connection with least one elongated stripe extended outside the anterior end of the applicator. Moreover, the method potentially additionally comprising steps of deflating the balloon and pulling said stripe and thus thrusting the balloon towards the posterior abdominal wall while or after ejecting said applicator. The role of the stripe is hence to ensure complete deflation of the balloon thus enabling its easy ejection throughout the applicator. It is acknowledged in this respect that the inflating tube may provide an effective means for ejecting the balloon.

It is according to another embodiment of the present invention wherein the method defined in any of the above comprising inter alia immobilizing the rim of the posterior mesh to the posterior abdominal wall utilizing a plurality of anchoring means.

It is according to another embodiment of the present invention wherein the method further comprising utilizing of at least one inflatable balloon thus providing a driving force for helically deploying the posterior mesh. This method comprising inter alia the following: (a) inserting said applicator throughout the hernia into the wall of the abdominal cavity; (b) releasing at least one mesh into said cavity while helically deploying the same, such that said mesh is laying in parallel to said wall; (c) inflating said balloon to a predetermined size, hence thrusting said mesh towards the posterior abdominal wall; (d) deflating said balloon and evacuating it throughout said applicator; and then (e), removing said applicator. Steps B and C are provided simultaneously, step B before C and vice versa.

It is according to another embodiment of the present invention wherein the method additionally comprising coordinating the steps of helically deploying the posterior mesh and inflating the balloon by means of utilizing a sleeve that is adapted to reversibly yet effectively envelop the posterior mesh.

Thus, a coordinated method may comprise the following: enveloping the posterior mesh and at least the anterior portion of the balloon with a sleeve; helically deploying said mesh while inflating a balloon such that the sleeve is sliding forwardly (anteriorly) and then ejecting said sleeve outside the abdominal cavity.

It is another object of the present invention to disclose a cost effective and novel implantable means for treating hernia. This therapeutic assembly comprising inter alia the following ingredients: (a) an elongate open-bored applicator having an anterior portion which is terminated outside the body, and a posterior portion, which is terminated with an orifice. This orifice or the same with a detachable member is adapted to be inserted via the hernia into the abdominal cavity. (b) At least one collapsible mesh rolled in the applicator. The mesh is adapted to be deployed helically when injected outside the applicator (i.e., posterior mesh). (c) Injecting means adapted to push the mesh throughout the open bore of the applicator via the said posterior orifice. The injecting means are comprised of a maneuverable pistol and a handle operating the same.

It is another embodiment of the present invention wherein inflating means adapted to inflate a 3D mesh, e.g., inflatable bladder-like mesh are provided (not shown in the figures). Those inflating means are continuing through the applicator outside the abdominal cavity, and utilized to inflate said mesh to a predetermined volume or shape.

It is another embodiment of the present invention wherein the perimeter of the collar is shorter than the perimeter of the mesh, such that a portion of the mesh's plane body is free of enveloping collar.

It is another embodiment of the present invention wherein the device is comprised of posterior and anterior collapsible meshes interconnected in their central portion by means of a connector. The connector may comprise an aperture reversibly covered by a plurality of overlapping wings.

It is another embodiment of the present invention wherein the mesh as defined in any of the above is in connection with least one stripe, extended outside the anterior end of the applicator such that by pulling said stripe, said mesh is effectively thrusted towards the posterior abdominal wall. The stripe is preferably yet not exclusively extended outside the anterior throughout an aperture of the connector and ensuring the deflation of the balloon after use.

It is another embodiment of the present invention wherein the device defined in any of the above is additionally comprised of at least one inflatable balloon located at the posterior end of the applicator. This balloon is providing an extra driving force for thrusting the helically deployed posterior mesh towards the posterior abdominal wall. The balloon is preferably in connection with inflating means comprising fluid injector and fluid tubing, interconnecting said injector to said balloon. The tubing is located inside the open bore of the applicator, and penetrated the mesh via its connector.

It is another embodiment of the present invention wherein the posterior mesh and the balloon are enveloped by a means of a sleeve, adapted to coordinate the helically deploying of the mesh with the balloon inflation. Preferably, this sleeve is ejected outside the body cavity by ejecting means located inside the open bore of the applicator.

It is another embodiment of the present invention wherein the mesh additionally comprising fastening means adapted to immobilize the posterior mesh to the posterior abdominal wall, the anterior mesh to the anterior abdominal wall or the connector to the hernia. At least a portion of the fastening means may be located in a site or sites selected from the plane body portion facing the posterior abdominal wall, the connector, the elastic rim (collar) or any combination thereof. It is another embodiment of the present invention wherein fastening means are selected from hooks, clips, catches, fasteners; wherein the fastening means are connected with said mesh directly or indirectly; and/or wherein the fastening means are connected with said mesh by means of a flexible or strainable strips.

Figure 1B:
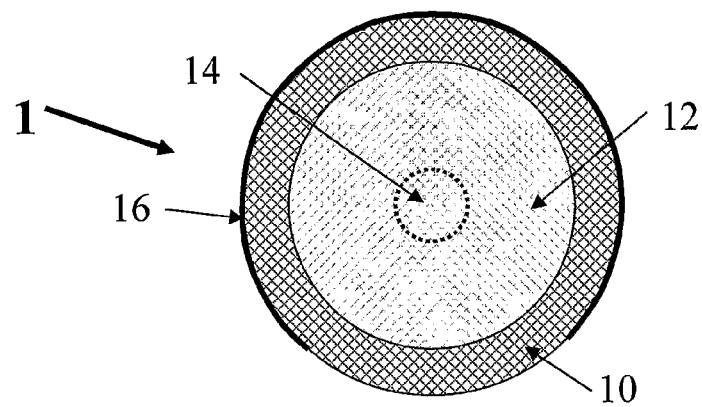
Figure 1C:
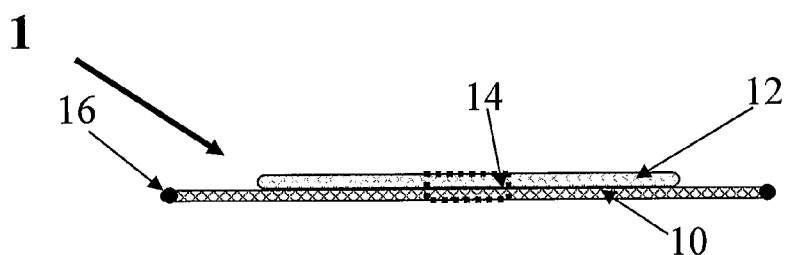
Figure 1D:
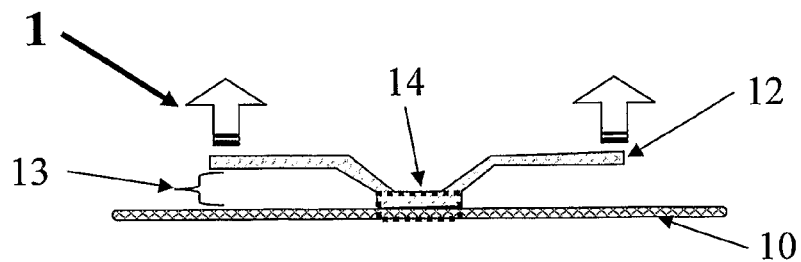

Reference is made now to FIG. 1a, schematically illustrating a perspective view of an implantable means for treating hernia according to one embodiment of the present invention (1) comprising two parallel thin meshes, interconnected by means of a radial connection. Connector (14) connects anterior mesh (12) and posterior mesh (10). Device (1) comprises an elastic, spring-like collar (16), not entirely enveloping the plane body of mesh (10). FIG. 1b presenting the same from a top view, demonstrating respectively small-diameter anterior mesh (12) and larger posterior mesh (10), wherein the ratio of their diameter may widely vary, e.g., from about 10:1 to 1:10. It is acknowledged in this respect that the shape of either of the meshes may be determined and adjusted before implanting the same. FIG. 1c schematically presenting a lateral cross section of the same, wherein FIG. 1d illustrates the same, wherein the rim of anterior mesh (12) is erected upwardly such that the two meshes are connected by means of connector (14).

Figure 2A:
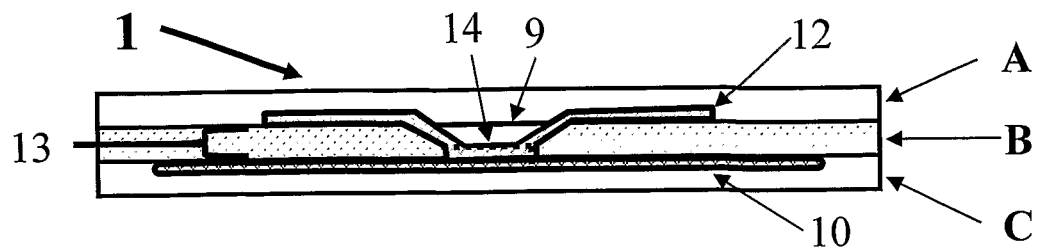
FIGS. 2a to 2b schematically present two meshes and their implementing view according to another embodiment of the present invention.
Figure 2B:
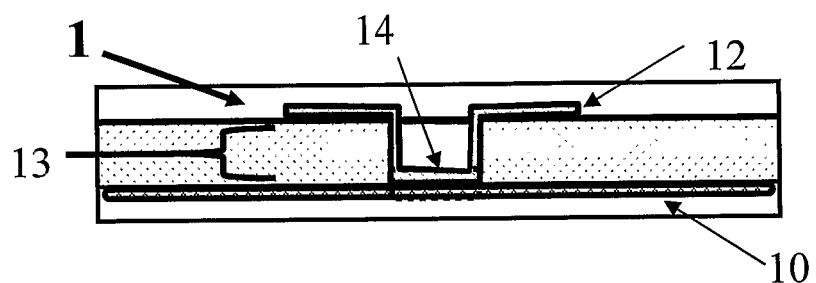

Reference is made now to FIGS. 2a and 2b, schematically illustrating lateral cross sections of the same, wherein mesh (10) is located between biological tissues B and C, and mesh (12) clasps between tissues (A) and (B). The hernia (9) between layers A and B is sealed by means of the novel two meshes infrastructure. It is acknowledged in this respect that the width and thickness of the biological tissues (A-C) and the hernia diameter may vary without significantly decreasing the effectiveness of the device (1). Either posterior or anterior meshes are flexible, and tolerate a wide scope of hernia systems, such as the case demonstrated in FIG. 2b.

Figure 3A:
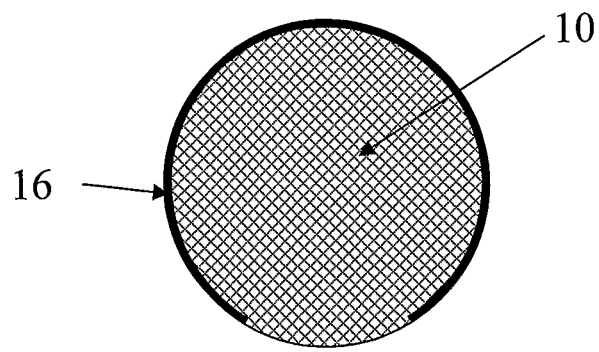
FIGS. 3a to 3d schematically present various meshes and collars according to another embodiment of the present invention.
Figure 3B:
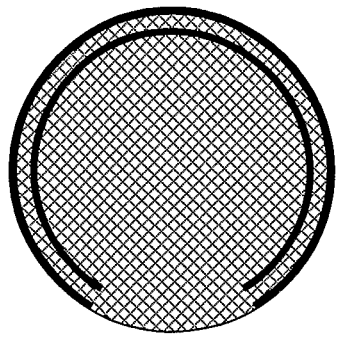
Figure 3C:
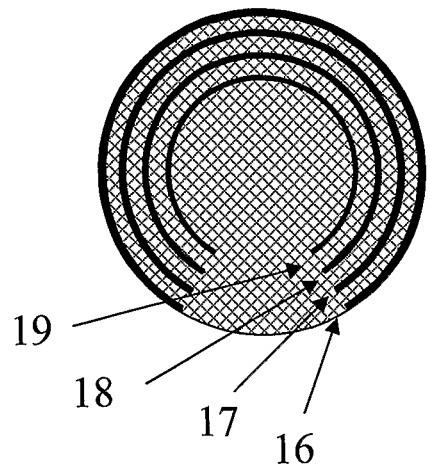
Figure 3D:
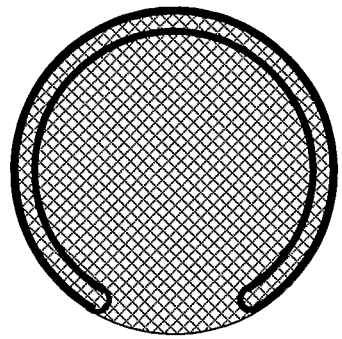
Figure 4A:
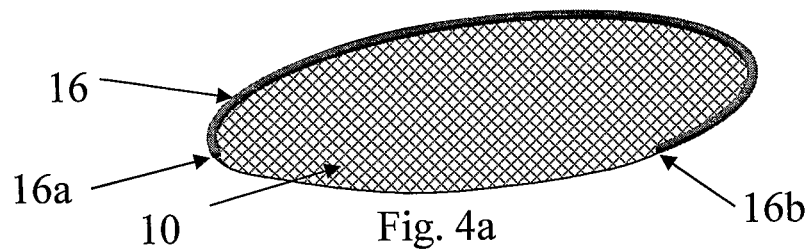
FIGS. 4a to 4d schematically present various mechanisms for rolling and collapsing said meshes and collars according to another embodiment of the present invention.
Figure 4B:
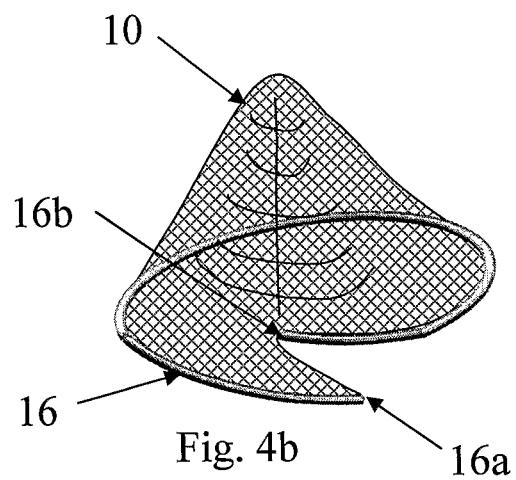
Figure 4C:
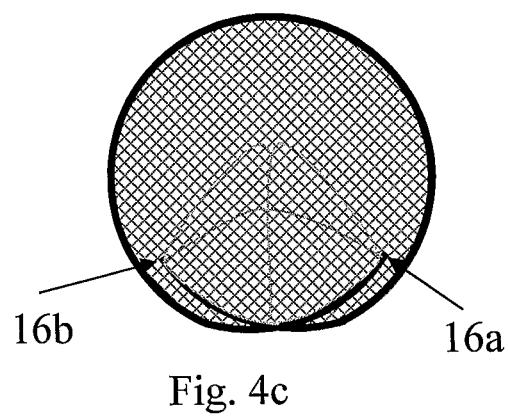
Figure 4D:
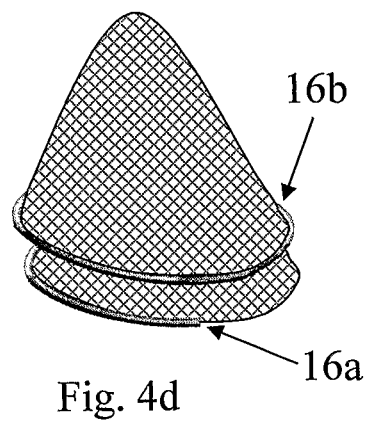

Reference is made now to FIGS. 3a and 3d, schematically illustrating top view of the implantable means for treating hernia according to another embodiment of the present invention. Collar (16) is presented in various modes. The portion of mesh (10) which is not enveloped is determined by various parameters, such as mesh's flexibility, size etc. Collar (16) may be utilized as single thin member (FIG. 3a), layered member (FIG. 3b-c), double layered member (FIG. 3d) etc.

Figure 5A:
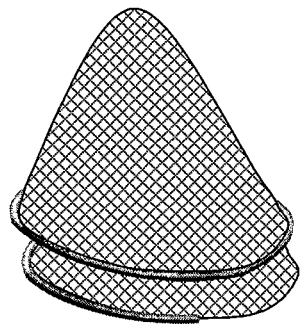
FIGS. 5a to 5c schematically present various mechanisms for helically rolling said meshes and collars according to another embodiment of the present invention.
Figure 5B:
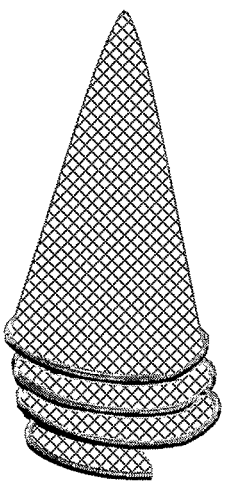
Figure 5C:
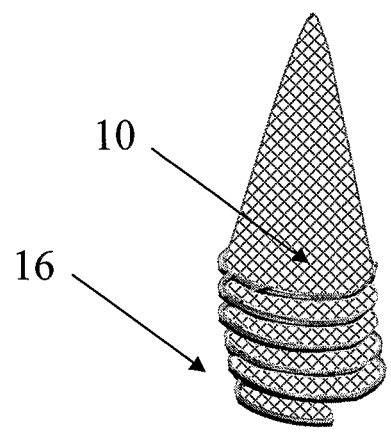

Reference is made now to FIGS. 4a to 4d, schematically illustrating perspective view of the implantable means for treating hernia according to another embodiment of the present invention, wherein collar (16) is rolled in a manner it deployed helically. Those examples are provided with few possible mechanisms to construct 3D cone-like mesh member from 2D flattened mesh. Various collapsing techniques are hence demonstrated, wherein other are also possible. FIG. 5 also presenting a schematic view of a helix-like rolled mesh, adapted to expend in a manner is perimeter is enlarged while it rotates, thus enabling the effective, smooth and rapid thrust of the mesh towards the posterior abdominal wall.

Figure 6A:
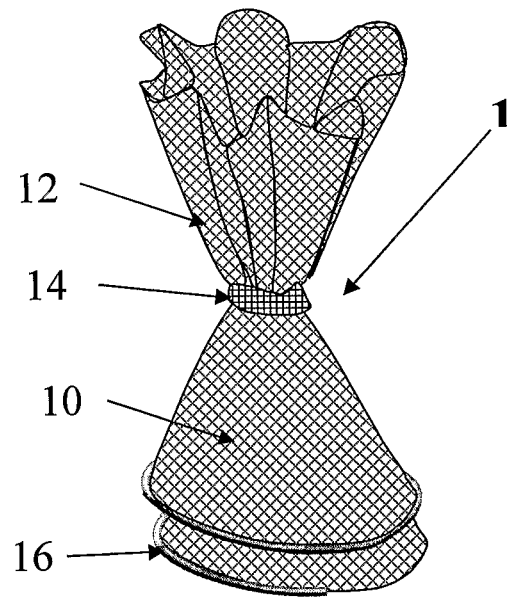

Reference is made now to FIGS. 6a and 6b, schematically illustrating a perspective view of the implantable means having two interconnected mesh layers according to another embodiment of the present invention. The posterior mesh (10) is loosely folded (FIG. 6a) such that flexible helix is directed to the posterior side of the hernia, wherein the anterior mesh (12) is folded in an opposite direction. Connection (14) interconnects the same. Right scheme, i.e., FIG. 6b presents the same in a helix-like tight rolling configuration such that the external diameter of the rolled mesh is significantly smaller than its diameter in its terminal open configuration.

Figure 7C:
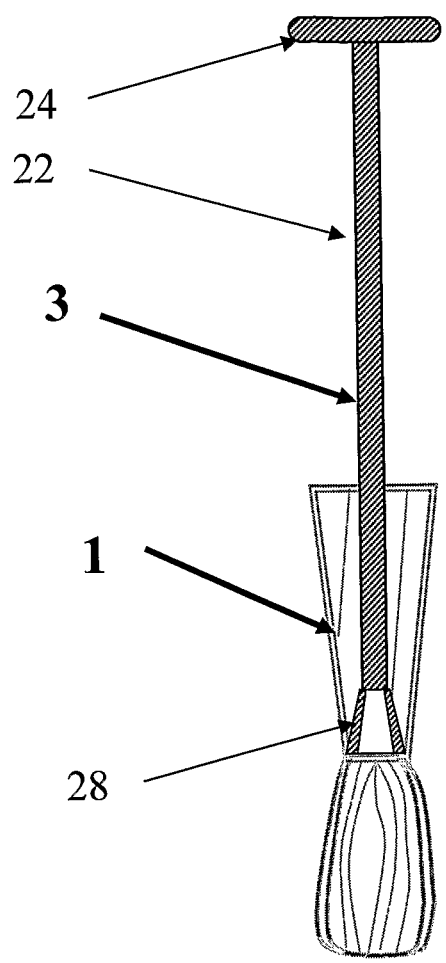

Reference is made now to FIGS. 7a to 7c, schematically illustrating a perspective and lateral cross sections of sterilizeable implantable means comprising an elongated applicator (2) with an open bore, wherein two interconnected mesh layers are rolled according to another embodiment of the present invention. This syringe-like applicator is comprised of injecting means comprising a handle (3) adapted for one hand use (24) wherein the piston axle (22) penetrates the applicator-rounded envelope (20) via opening (26). Aperture 21 is especially provided for feeding fluids, chemicals, lubricants, glues, biocides etc into or onto the hernia. The two meshes may by assembled by a means of joint or connector (28).

Figure 8A:
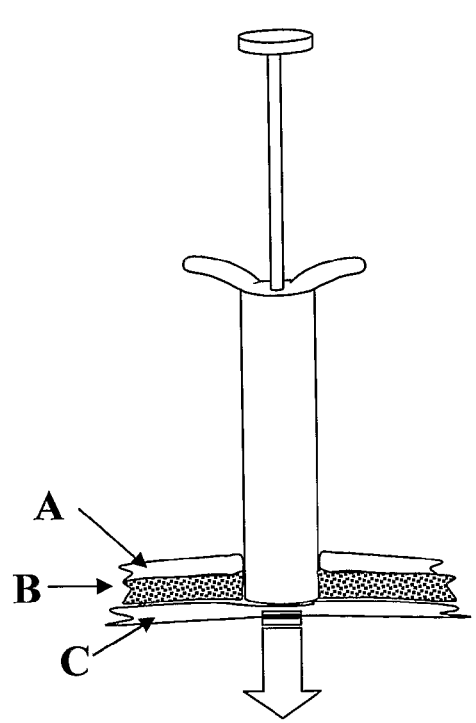
FIGS. 8a to 8f schematically present a method of helically deploying a plurality of meshes according to another embodiment of the present invention.
Figure 8B:
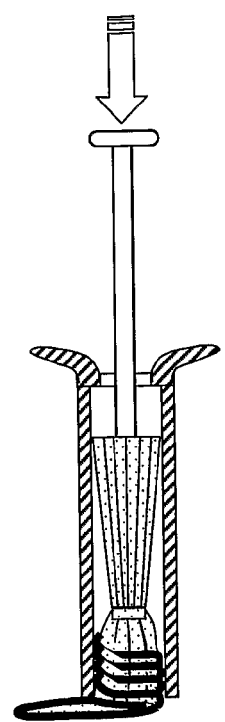
Figure 8C:
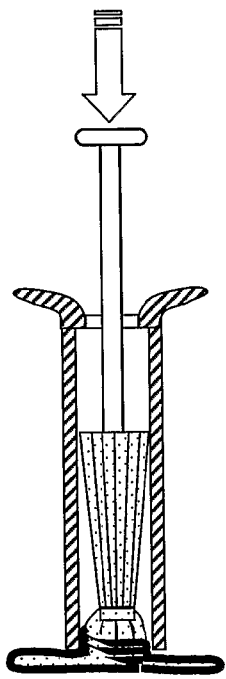
Figure 8D:
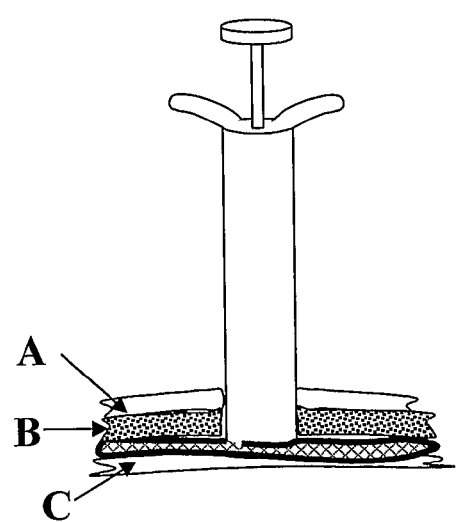
Figure 8E:
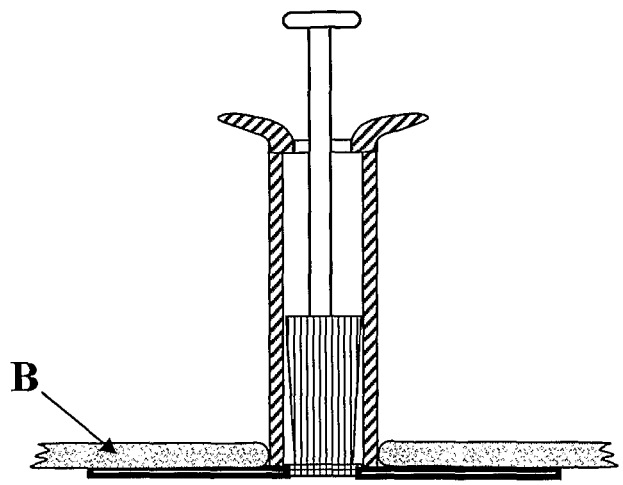
Figure 8F:
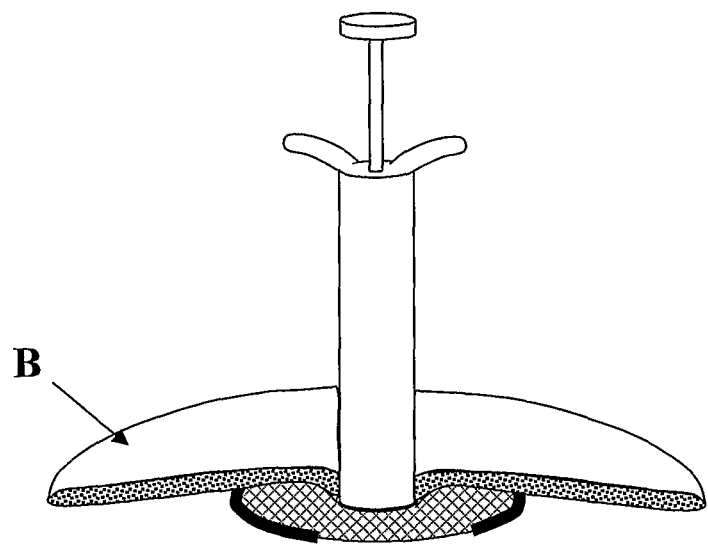

Reference is made now to FIGS. 8a and 8f, schematically illustrating a perspective view and lateral cross sections of a method of treating hernia by means of implantable applicator comprising two interconnected mesh layers according to another embodiment of the present invention. The applicator is initially inserted into the hernia (FIG. 8a) such that its posterior orifice is located between two predetermined tissues (A and C). The posterior mesh is helically deployed (FIGS. 8b-8f) such that it protruded in the body along the layers, and situated itself tightly between layers B and C.

Figure 9A:
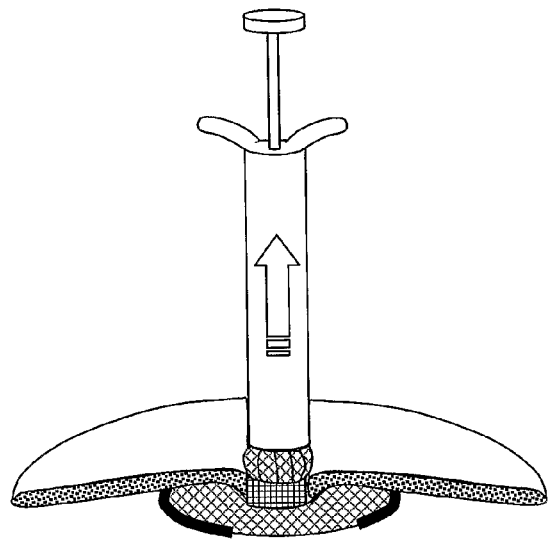
FIGS. 9a to 9c schematically present the role of the anterior mesh according to another embodiment of the present invention.
Figure 9B:
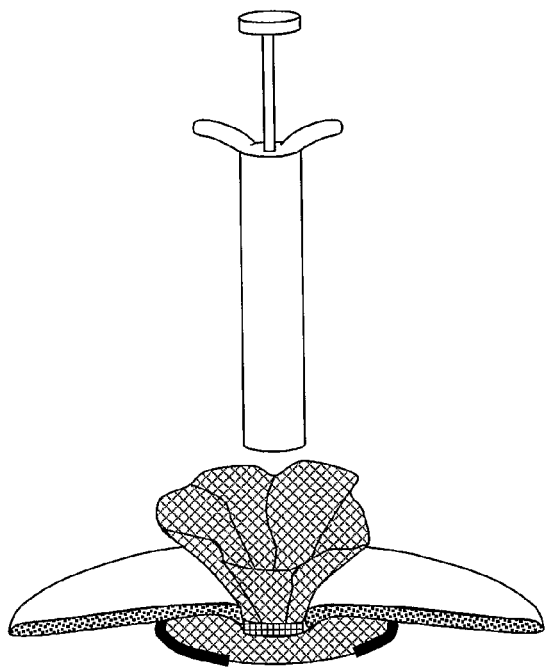
Figure 9C:
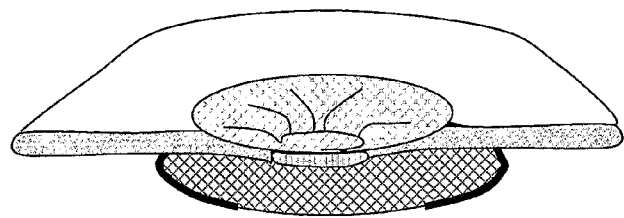

Reference is made now to FIGS. 9a and 9c, schematically illustrating a perspective views of the implantable means according to another embodiment of the present invention. The role of the anterior mesh is hereby presented, wherein maneuvering the pistol of the applicator backwardly; the anterior mesh is ejected, lying parallel to the abdominal wall, sealing hermetically the hernia opening.

Figure 10A:
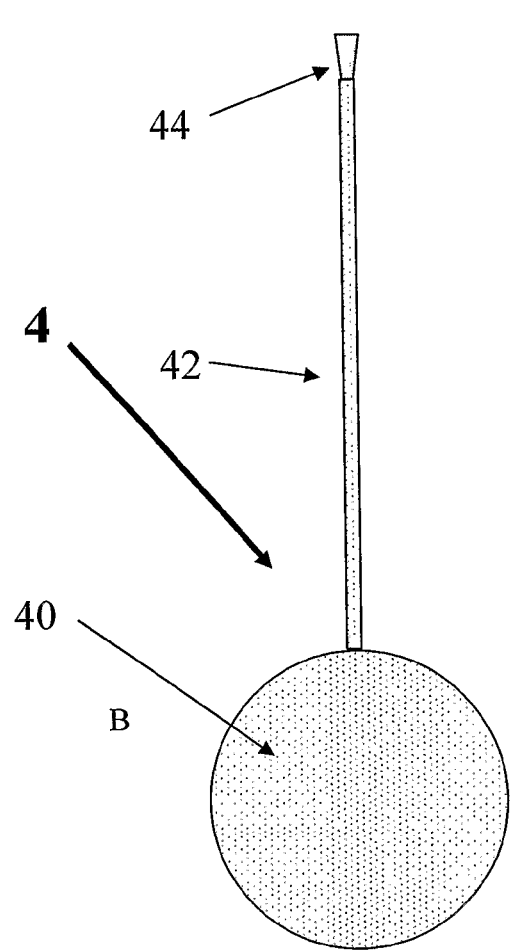
FIGS. 10a to 10h schematically present the structure-function role of the inflated balloon and the meshes' connector according to another embodiment of the present invention.
Figure 10B:
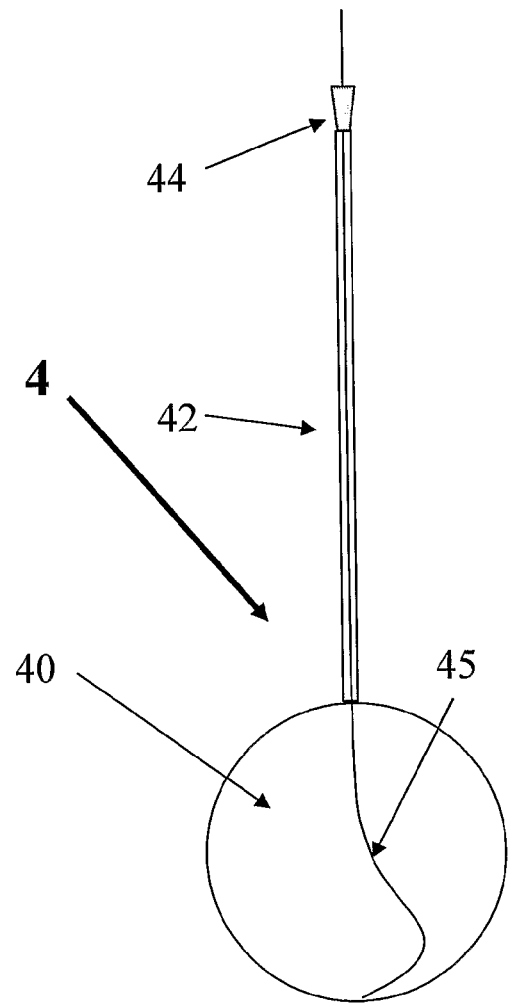
Figure 10C:
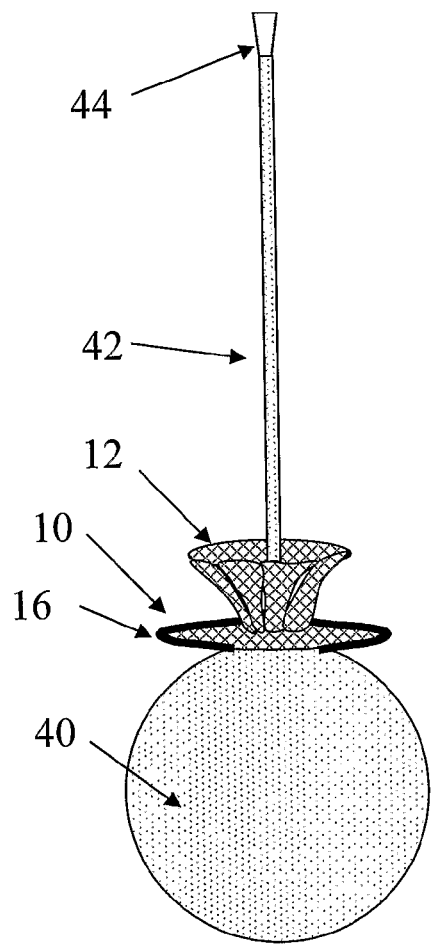
Figure 10D:
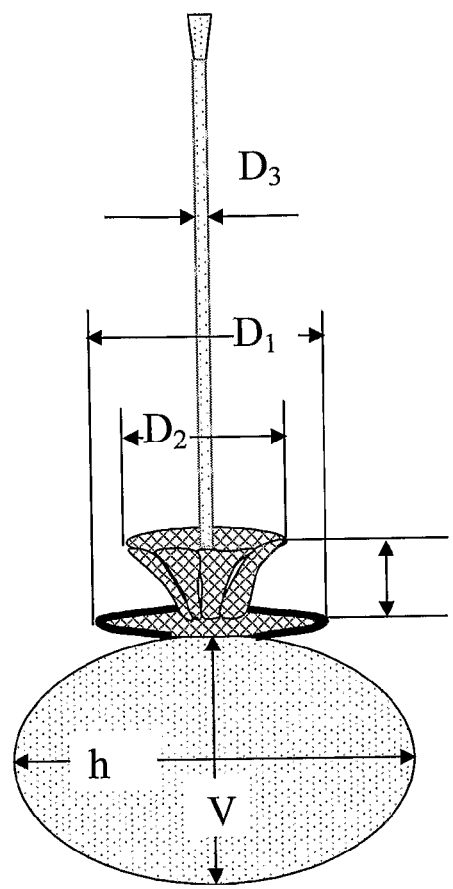
Figure 10E:
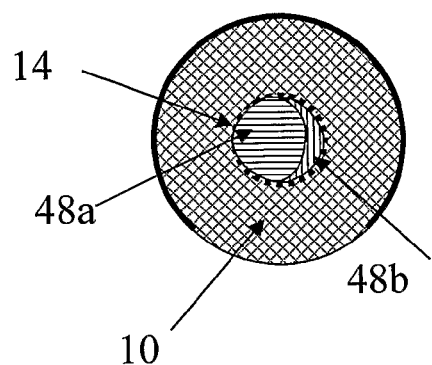
Figure 10F:
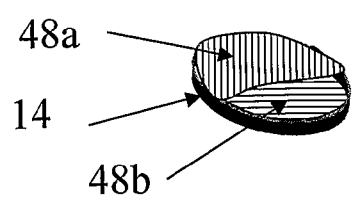
Figure 10G:
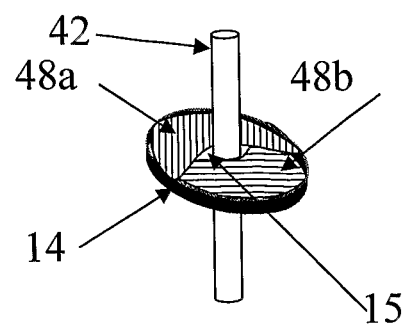
Figure 10H:
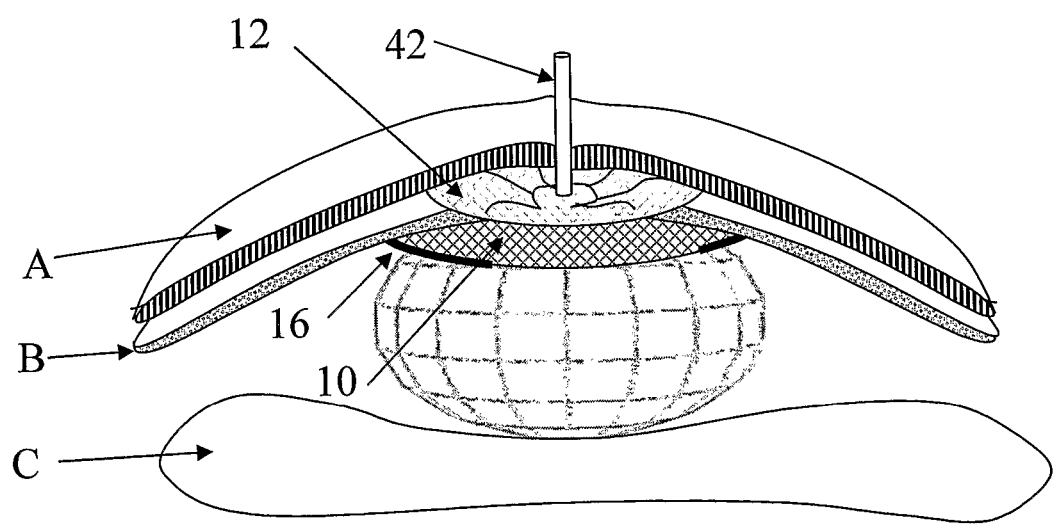

Reference is made now to FIGS. 10a and 10h schematically illustrating one method of utilizing a balloon as a driving force for helically deploying the posterior mesh according to another embodiment of the present invention. The balloon comprising an inflatable portion (40), fluid tubing (42) and a liquid anterior orifice (44). This method is comprising the step of applying at least one stripe (45), said stripe is immobilized to the balloon inner portion and loose free at the anterior end of the applicator (44), such that by pulling the stripe deflated balloon is ejected outside the applicator in a collapsed manner. The proportions of the two meshes (10, 12), collar (16) and balloon may widely vary; especially their external diameter may be of various ratios. Views 10e to 10g present one possible mode of the sealed connector, adapted to comprise inflation tube (42), by comprising overlapping wings of both upper and lower meshes. View 10h presents a perspective illustration of the same. The balloon is shown to provide an effective foundation and driving force for thrusting the posterior mesh forwardly.

Figure 11:
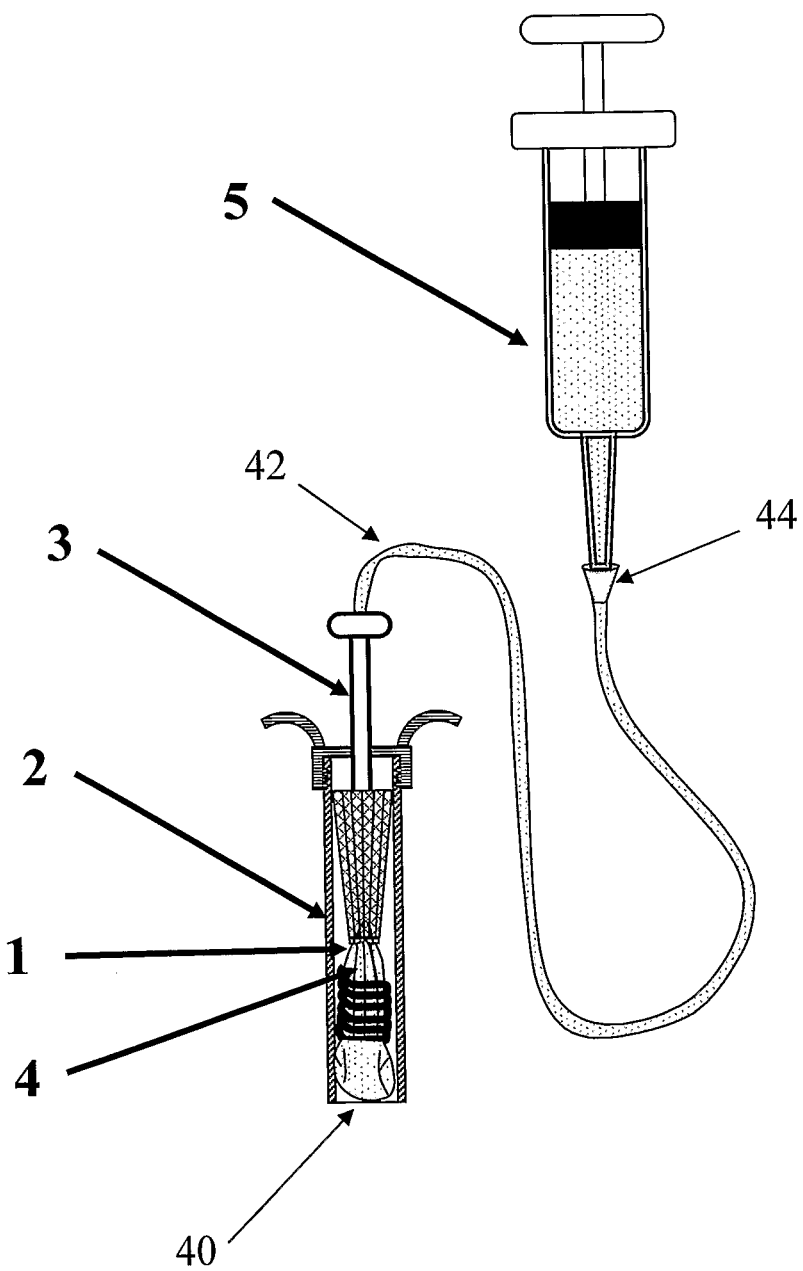
FIG. 11 schematically presents an imp lamentable assembly (applicator and inflating means) according to another embodiment of the present invention.

Reference is made now to FIG. 11, schematically illustrating a perspective view of the implantable assembly according to another embodiment of the present invention. This assembly comprises the applicator (1-4) as defined in any of the above, a balloon inflating tubing (42), and inflating means comprising inter alia a syringe (5) and tubing connector (44).

Figures 12A, 12B:
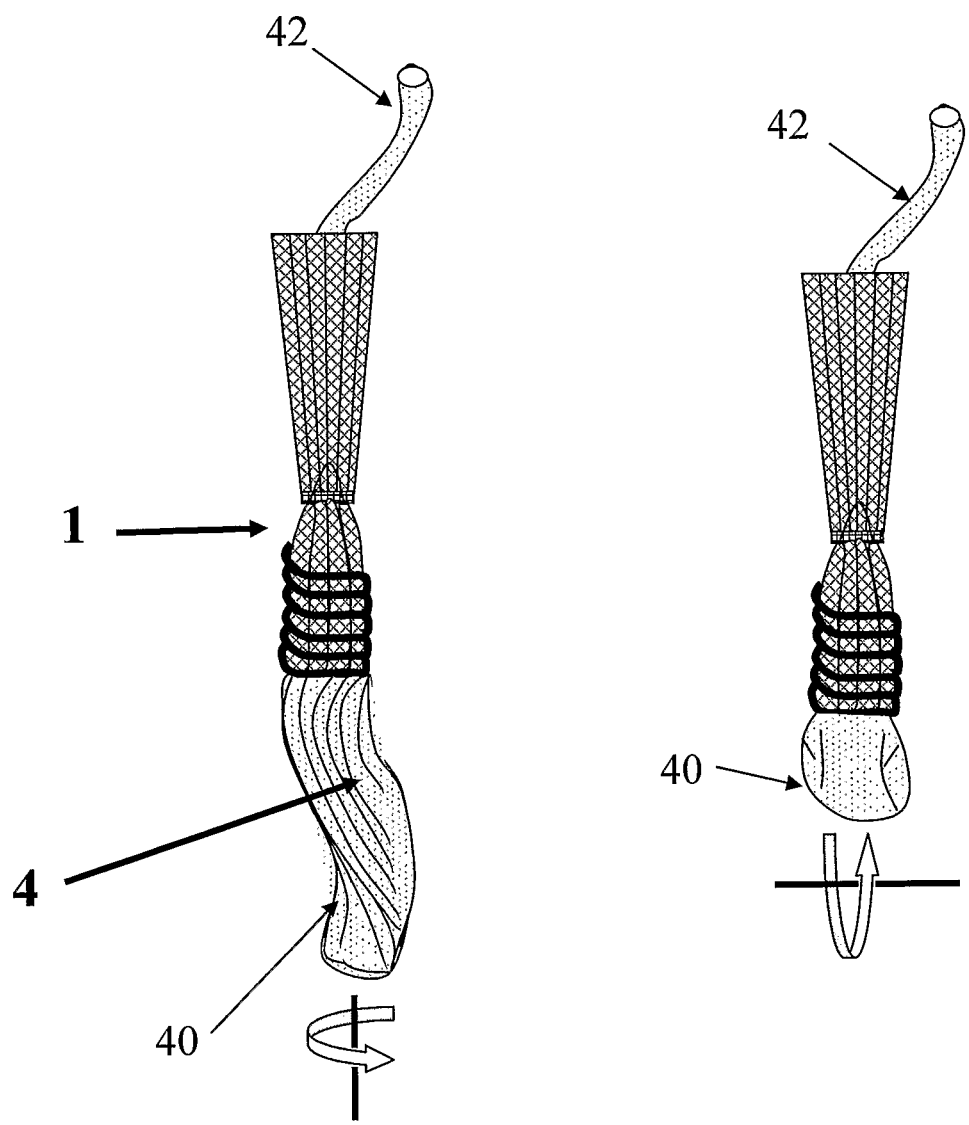
FIGS. 12a to 12b schematically present the balloon-meshes assembly according to another embodiment of the present invention.

Reference is made now to FIGS. 12a-12b, schematically illustrating a perspective views and a cross section of the implantable assembly according to another embodiment of the present invention. Those schemes present the folding-deployment mechanism of balloon 40 in respect to the helically rolled posterior mesh. The inner diameter of the pistol handle (3) and the inner diameter of balloon's inflating tubing 42 is adapted to be wide enough that the deflated balloon can be collapsed and ejected outside the applicator via the pistol handle.

Figure 13A:
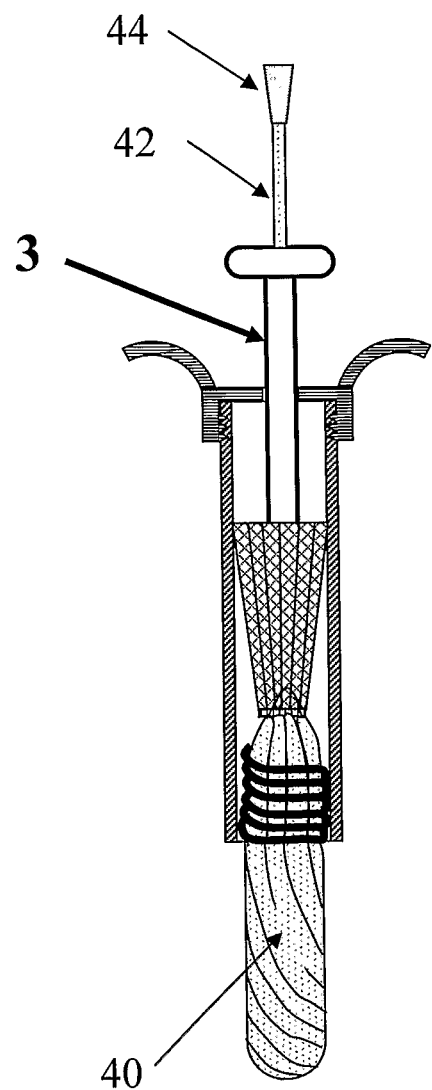
FIGS. 13a to 13c schematically present the mechanism of balloon inflating and mesh' helically deployment according to another embodiment of the present invention.
Figure 13B:
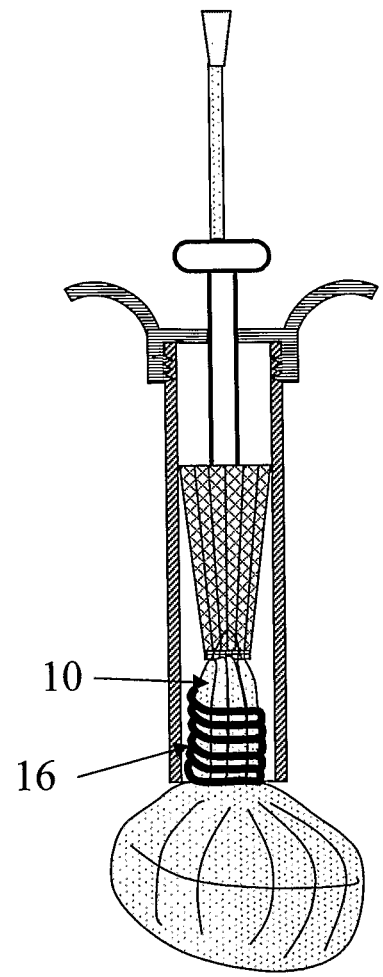
Figure 13C:
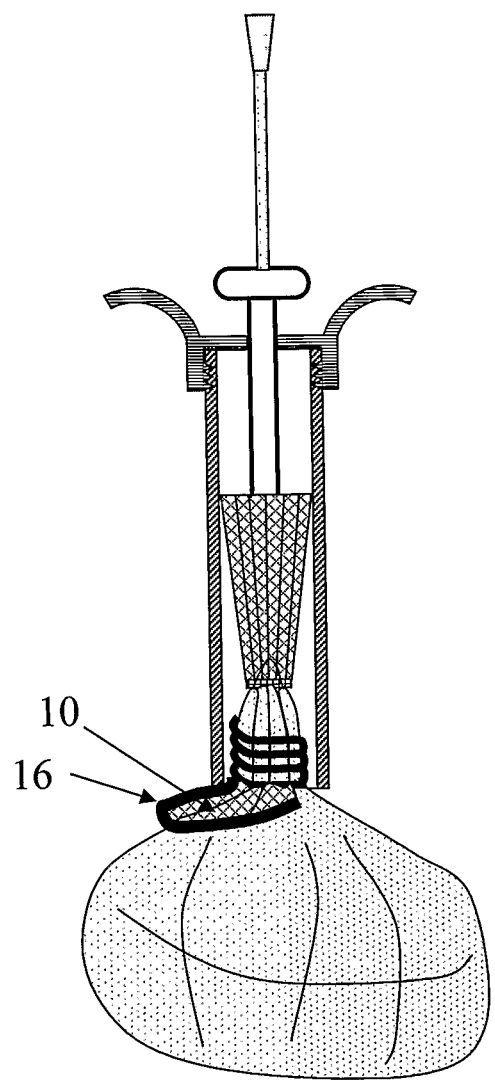
Figure 14A:
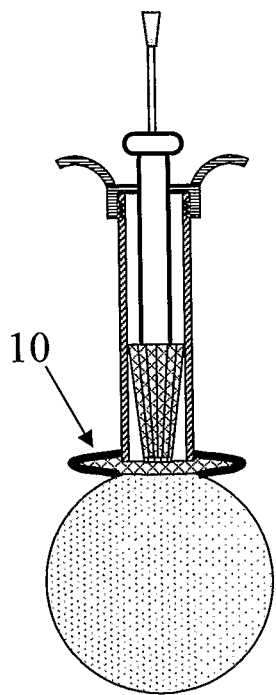
FIGS. 14a to 14d schematically present the mechanism of balloon inflating and mesh' helically deployment with removable applicator according to another embodiment of the present invention.
Figure 14B:
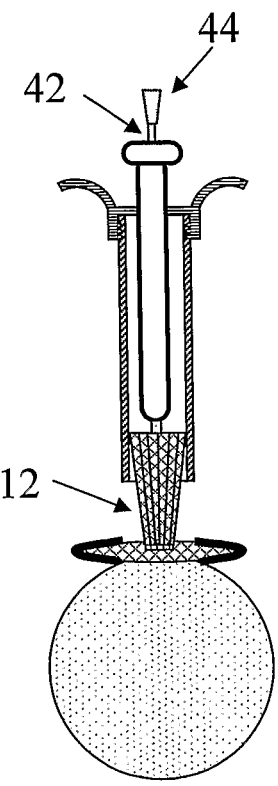
Figure 14C:
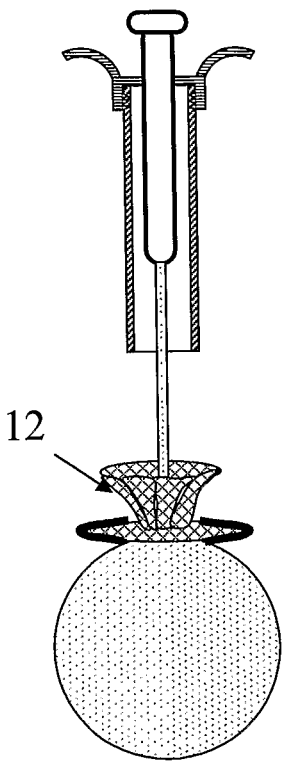
Figure 14D:
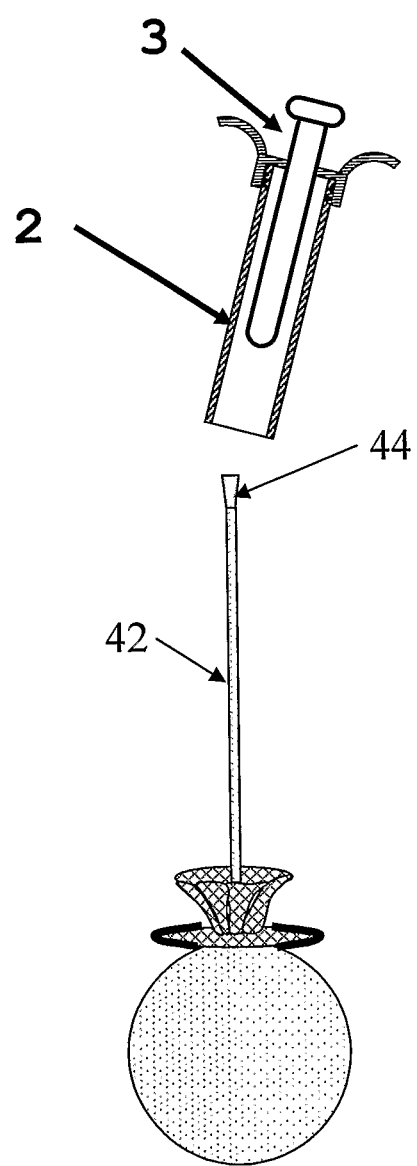
Figure 16A:
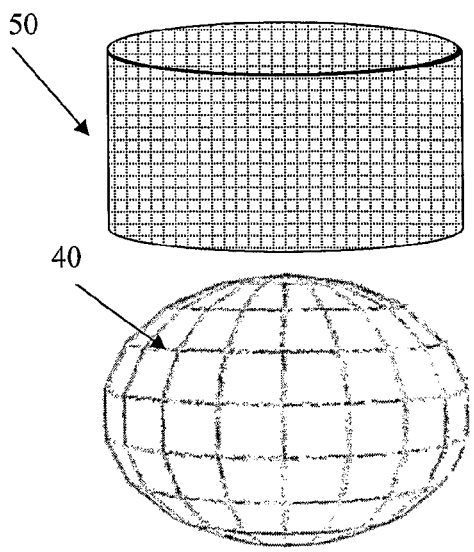
FIGS. 16a to 16d schematically present sleeve attached to the balloon perimeter according to another embodiment of the present invention.
Figure 16B:
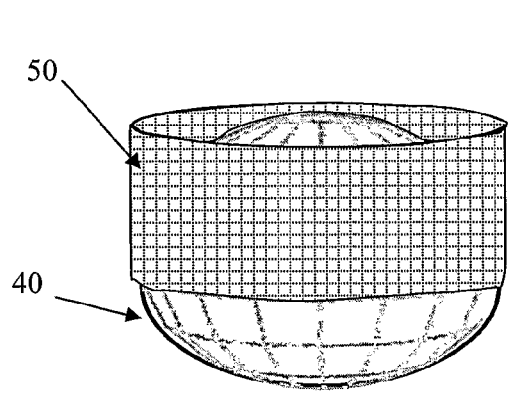
Figure 16C:
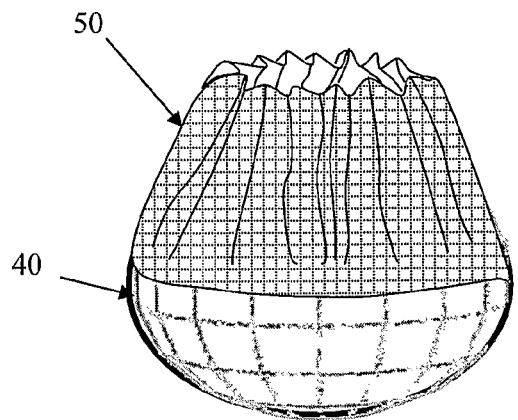
Figure 16D:
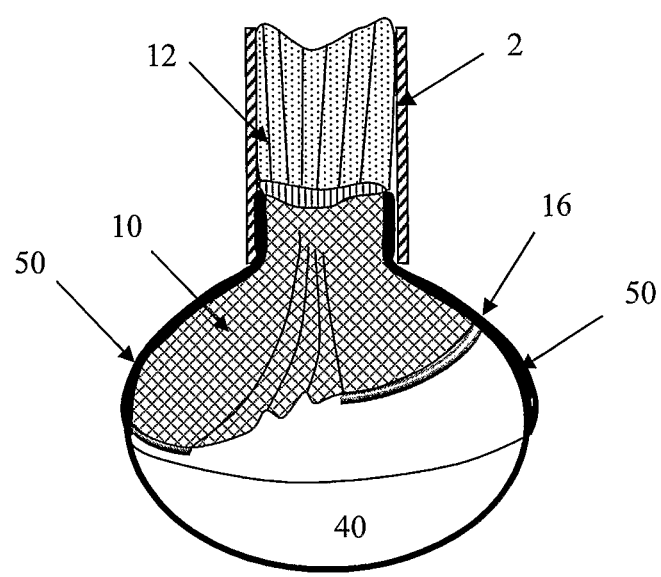

Reference is made now to FIGS. 13a-13c, schematically illustrating lateral cross sections of the implantable assembly according to another embodiment of the present invention. Those schemes demonstrate the incorporated mechanism of the implant assembly, specifically presenting the inflation of the balloon and then the helical deployment of posterior mesh.

Reference is made now to FIGS. 14a to 14d, schematically illustrating cross sections of the implantable assembly according to another embodiment of the present invention. Those schemes show that after inflating the balloon and deploying the two meshes (10, 12), applicator (2, 3) is removed. This assembly thus comprise a non-return valve (44) retaining the inflating fluid inside the balloon and its tubing (42).

Reference is made now to FIGS. 15a to 15c, schematically illustrating fastening means (18, 19, 19a) e.g., nail-like, tooth-like, screw-like fasteners according to another embodiment of the present invention. Those fastening means are of various sizes, shapes and fastening mechanisms. Usually yet not exclusively the fastening means are located on the collar portion (16) of the device. Those fastening means may be directly or indirectly (19b) immobilize to the collar.

Figure 17C:
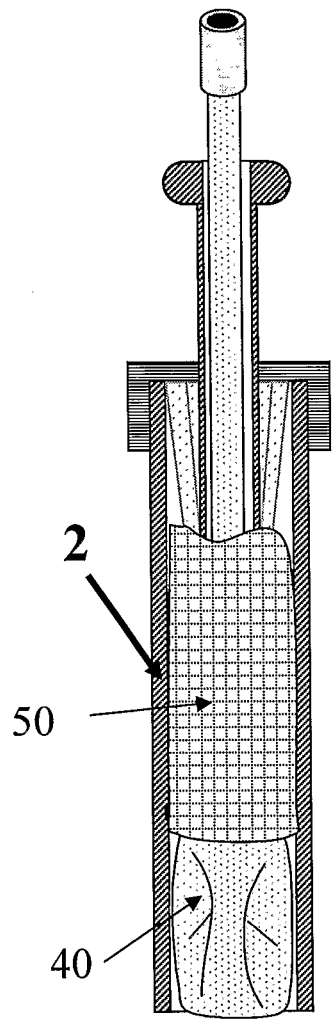
Figure 18A:
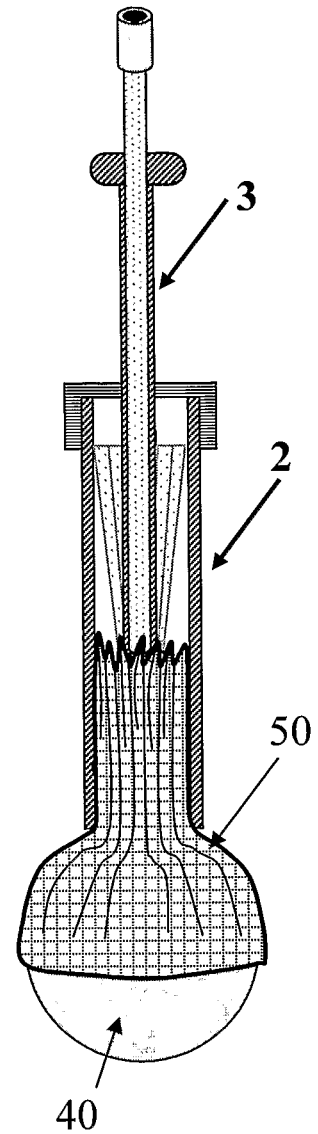
Figure 18B:
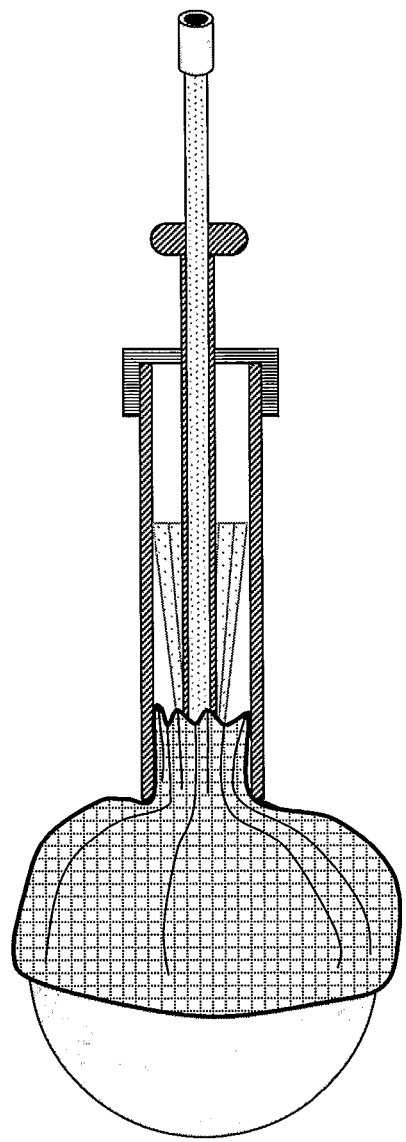
Figure 18C:
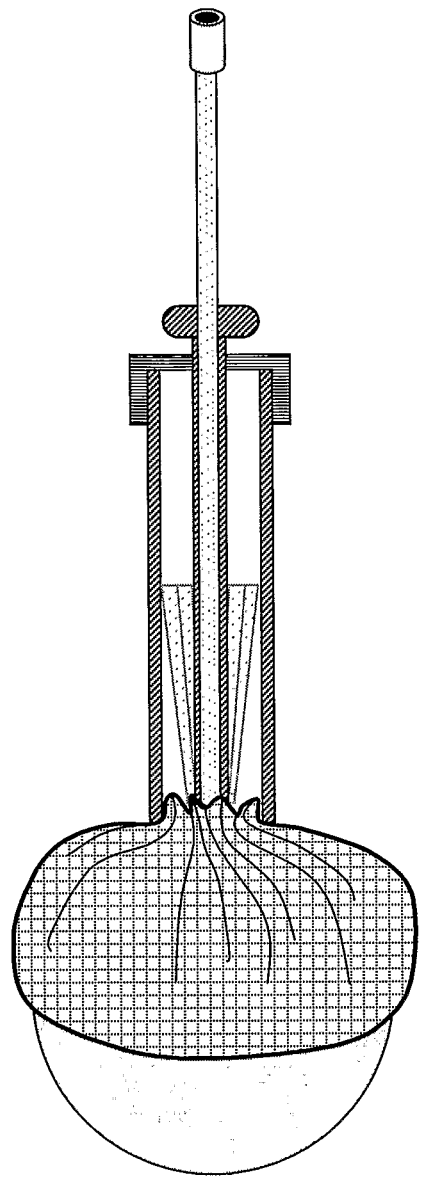
Figure 18D:
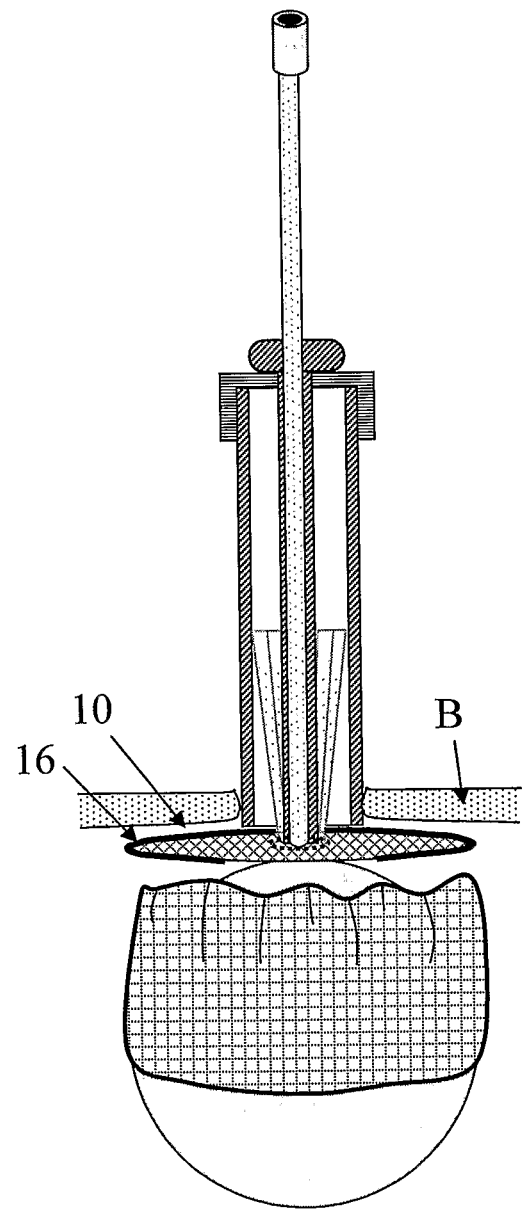

Reference is made now to FIGS. 16a to 16d, schematically illustrating coordinating sleeve (50) according to another embodiment of the present invention. Hence, for example, sleeve 40 is enveloping balloon 50 such that the steps deployment of mesh 10 and inflation of balloon 40 are coordinated at time. Reference is made to FIG. 17a to 17c, presenting the method of coordinating or sustaining either the deployment of mesh 10, and/or balloon 40 by means of sleeve 50 located in the applicator shall (2). Lastly, reference is made to FIGS. 18a to 18d showing the same method and coordinating/sustaining means and the various implementing process.

The invention claimed is:

1. A hernia repair device, comprising:
an inflatable balloon having an inflation tube configured to inflate the balloon, a first side and a second side; and
a hernia repair patch having a first reduced configuration for insertion into a body in which the balloon is at least partially deflated and a second deployed configuration in which the hernia repair patch has a planar shape for deployment at a hernia site when the balloon is inflated, the hernia repair patch being removably attached to said balloon such that, when the hernia repair patch is in the second deployed configuration, the hernia repair patch is situated only on the first side of said balloon, the second side of the balloon is exposed and the inflation tube passes through the hernia repair patch;
wherein inflation of the balloon, at least in part, causes the hernia repair patch to move from the first reduced configuration to the second deployed configuration; and
wherein the balloon is configured to be detached from the hernia repair patch and removed from the body.

2. The hernia repair device according to claim 1, wherein said hernia repair patch comprises an elastic rim.

3. The hernia repair device according to claim 2, wherein said elastic rim is shorter than a perimeter of said hernia repair patch.

4. The hernia repair device according to claim 1, wherein said balloon provides a driving force for said hernia repair patch.

5. The hernia repair device according to claim 1, further comprising: a second hernia repair patch removably attached to said balloon.

6. The hernia repair device according to claim 5, wherein said hernia repair patch and second hernia repair patch are interconnected in their central portions.

7. The hernia repair device according to claim 5, wherein a diameter of said second hernia repair patch is smaller than a diameter of said hernia repair patch.

8. The hernia repair device according to claim 7, wherein a ratio of the diameters of the hernia repair patch and second hernia repair patch is 10:1.

9. The hernia repair device of claim 1, wherein the hernia repair patch is rolled in the first reduced configuration.

10. The hernia repair device of claim 1, wherein the hernia repair patch is a two-dimensional sheet-like member.

11. The hernia repair device of claim 1, wherein the hernia repair patch in the second deployed configuration is substantially non-conformal with the balloon when inflated.

12. The hernia repair device of claim 1, wherein the hernia repair patch is formed of a mesh.

13. The hernia repair device of claim 1, further comprising an inflator coupled to the inflation tube for inflating the balloon.

14. The hernia repair device of claim 1, further comprising an elongated member coupled to the balloon and configured to detach the balloon from the hernia repair patch.

15. A hernia repair device, comprising:
an inflatable balloon having an inflation tube configured to inflate the balloon; and
a hernia repair patch having a first reduced configuration for insertion into a body in which the balloon is at least partially deflated and the hernia repair patch is rolled, and a second deployed configuration in which the hernia repair patch has a planar shape for deployment at a hernia site when the balloon is inflated, the hernia repair patch being removably attached to said balloon such that, when the hernia repair patch is in the second deployed configuration, the hernia repair patch is situated only on one side of said balloon and the inflation tube passes through the hernia repair patch;
wherein inflation of the balloon, at least in part, causes the hernia repair patch to move from the first reduced configuration to the second deployed configuration; and
wherein the balloon is configured to be detached from the hernia repair patch and removed from the body.

16. The hernia repair device of claim 15, wherein in the first reduced configuration, the hernia repair patch is configured to be held in a rolled shape in an applicator.

\* \* \* \* \*